United States Patent [19]

Garcia et al.

[11] Patent Number: 4,533,322
[45] Date of Patent: Aug. 6, 1985

[54] DENTAL INSTRUMENT LIGHT

[75] Inventors: Philippe Garcia, Besancon; Michel Seigneurin, Douvaine, both of France

[73] Assignee: Micro-Mega, Besancon, France

[21] Appl. No.: 578,278

[22] Filed: Feb. 8, 1984

[30] Foreign Application Priority Data

Feb. 8, 1983 [FR] France ................ 83 02092

[51] Int. Cl.³ .............................................. A61C 3/00
[52] U.S. Cl. ...................................................... 433/29
[58] Field of Search ........................................... 433/29

[56] References Cited

U.S. PATENT DOCUMENTS

| 4,330,274 | 5/1982 | Friedman et al. | 433/29 |
| 4,334,863 | 6/1982 | Magid et al. | 433/29 |
| 4,375,964 | 3/1983 | Knopp et al. | 433/29 |
| 4,398,885 | 8/1983 | Loge et al. | 433/29 |
| 4,403,957 | 9/1983 | Mossle et al. | 433/29 |
| 4,477,252 | 10/1984 | Lieb et al. | 433/29 |

FOREIGN PATENT DOCUMENTS

| 1123034 | 9/1956 | France | 433/29 |
| 1161157 | 8/1958 | France | 433/29 |
| 1412622 | 11/1975 | United Kingdom | 433/29 |

Primary Examiner—John J. Wilson
Attorney, Agent, or Firm—Robert E. Burns; Emmanuel J. Lobato; Bruce L. Adams

[57] ABSTRACT

A device for supplying luminous energy to a dental instrument to illuminate the area of treatment on a tooth being treated. The luminous energy is applied from a bulb housed in the device through an optical fiber extending through the dental instrument and having an end disposed for receiving the luminous energy from the bulb. Provision is made for energizing the bulb when the device is mounted on an electrical supply cable. A contact arrangement of two conductive studs disposed in a bore of an insulating sleeve and axially biased by a conductive spring to extend from the bore provides for making contact between the bulb and supply cable when the device is mounted on the supply cable. A section of the bore of the sleeve between the ends of the sleeve defines shoulders limiting the axial travel of the studs which have enlarged ends for engaging the shoulders.

3 Claims, 1 Drawing Figure

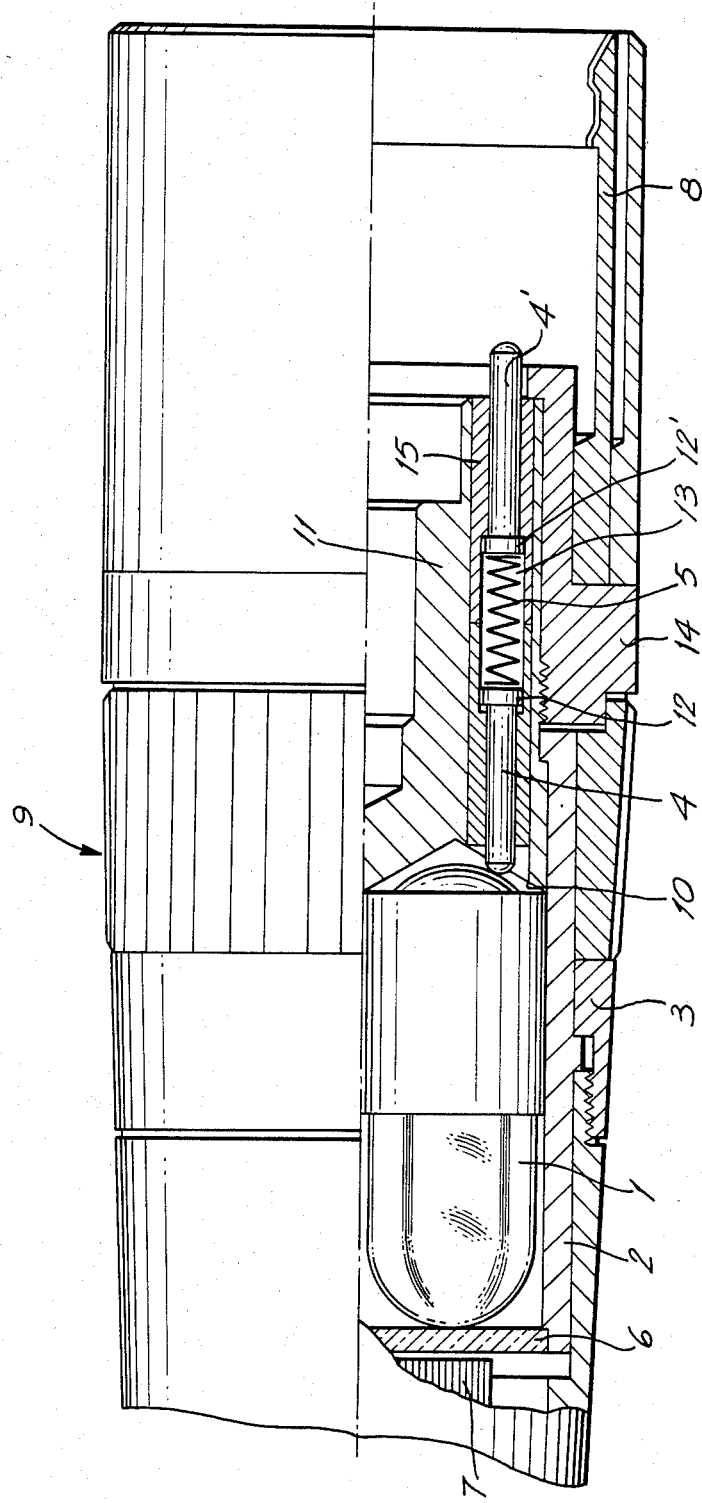

DENTAL INSTRUMENT LIGHT

BACKGROUND OF THE INVENTION

The present invention relates to a device for supplying luminous energy to a dental instrument to illuminate the area of treatment on the tooth, the luminous energy being transmitted from an electric bulb by an optical fibre passing through the instrument, the said instrument being connected in use on the head of a supply cable.

In general, in the known devices, the light is produced by an electric bulb arranged in the head of the cable supplying the instrument. At the time of the coupling, this bulb illuminates an optical fibre arranged in the instrument. Such a device is, for example, the subject of French Application No. 81/15,851.

This device, however, has the disadvantage of being fragile. It requires, moreover, a complex switching and intensity control unit.

The present invention is aimed at overcoming these disadvantages.

SUMMARY OF THE INVENTION

According to the invention, this result is obtained with a device for supplying luminous energy to a dental instrument to illuminate the area of treatment on the tooth, the luminous energy is transmitted from an electric bulb by an optical fibre passing through the instrument, the instrument is connected in use to the head of a supply cable, characterised in that the bulb is arranged inside the instrument.

According to an advantageous embodiment, the electrical supply to the bulb will operate from the time of coupling of the instrument on the head of the cable by a contact becoming connected to the electrical energy supply of the cable.

Advantageously, this contact will be produced by two studs separated from each other by a conductive spring, so as to ensure a perfect contact in use under all conditions.

BRIEF DESCRIPTION OF THE DRAWING

The invention will be better understood with the aid of the following description of a non-limiting embodiment, with reference to the attached single drawing which is a view in lengthwise cross-section of a device according to the invention.

DESCRIPTION OF THE PREFERRED EMBODIMENT

The electric bulb (1) is arranged inside the instrument (9), in a casing (2) which is capable of being disassembled by means of a nut (3).

One phase of the bulb is supplied by an earth contact on the casing (2). The other contact is produced by a system of two studs (4, 4') arranged in an insulating sleeve (15), the studs being separated from each other by a conductive spring (5). This arrangement makes it possible to take up the differences in length of the bulbs and to obtain a perfect contact, which is at optimum on every occasion.

The front face of the bulb is protected by a transparent disc (6), which can assume any form whatsoever which enables it to increase the efficiency of the illumination (for example, a lens). This disc is arranged at the end of the above-mentioned casing (2).

The bulb (1) abuts against the disc (6). At its other end it bears on a dish (10) of a seat (11). This seat (11) receives in a bore the studs (4, 4') whose widened ends (12, 12') are capable of moving in a housing (13) under the effect of the spring (5). The seat (11) is screwed into a retaining ring (14).

The light is conducted towards the working area from the bulb (1) by means of an optical fibre (7), or any other equivalent guide.

The rear of the instrument is arranged in a conventional manner to receive the head of the cable on which the instrument is held locked by any conventional system whatsoever, which transmits the electrical energy to the stud (4') when fastened, for example, by a socket (8).

We claim:

1. A device for supplying luminous energy to a dental instrument to illuminate an area of treatment on a tooth comprising, an electric bulb in the instrument, means for connecting the instrument to a head of an electrical energy supply cable, an optical fiber extends through the instrument having an end disposed for receiving luminous energy from the bulb for transmission therethrough, contact means for energizing the bulb immediately upon connection to the cable, the contact means comprising two conductive studs disposed separated from each other, a conductive biasing spring elastically separating the two studs, an insulating sleeve, and said studs being disposed axially spaced within said sleeve and said spring disposed in said sleeve maintaining the studs axially biased apart.

2. A device for supplying luminous energy to a dental instrument to illuminate an area of treatment on a tooth according to claim 1, including within said insulating sleeve a bore having a section with an enlarged cross section between the ends of the bore, each said stud having an enlarged end within said section for axial movement within said bore, and the enlarged end of each stud limiting axial travel of the studs apart from each other within the section of the bore of said sleeve, means defining a seat at one end of said bore on which said bulb is seated, one of said stubs biased extending into said seat for making electrical contact with said bulb when seated in said seat, and the other of said studs resiliently biased for extending axially out of said bore for effecting electrical contact when the device is connected to said supply cable.

3. A device for supplying luminous energy to a dental instrument to illuminate an area of treatment on a tooth according to claim 2, including a retaining ring holding said seat in the device.

* * * * *